United States Patent [19]

Fong et al.

[11] Patent Number: 5,536,889
[45] Date of Patent: Jul. 16, 1996

[54] PROCESS FOR THE TWO-STAGE HYDROGENATION OF METHYL ESTERS

[75] Inventors: Howard L. Fong, Sugar Land; David M. Singleton, Houston, both of Tex.; Richard E. Robertson, Baton Rouge, La.

[73] Assignee: Shell Oil Company, Houston, Tex.

[21] Appl. No.: 536,718

[22] Filed: Sep. 29, 1995

[51] Int. Cl.$^6$ .................... C07C 29/149; C07C 31/125
[52] U.S. Cl. .................................................... 568/885
[58] Field of Search ............................................ 568/885

[56] References Cited

U.S. PATENT DOCUMENTS

| | | | |
|---|---|---|---|
| 2,863,928 | 12/1958 | Indert | 568/885 |
| 4,380,657 | 4/1983 | Slaugh | 549/509 |
| 4,417,000 | 11/1983 | Slaugh | 518/713 |
| 4,565,803 | 1/1986 | Schoenthal et al. | 502/303 |
| 4,728,671 | 3/1988 | Hinnekens | 549/503 |
| 4,851,593 | 7/1989 | Gilbert | 568/864 |
| 5,001,284 | 3/1991 | Dupont | 568/885 |
| 5,004,845 | 4/1991 | Bradley et al. | 568/885 |
| 5,043,485 | 8/1991 | Fleckenstein et al. | 568/885 |
| 5,120,700 | 6/1992 | Matsuda et al. | 502/329 |
| 5,124,491 | 6/1992 | Fleckenstein et al. | 568/885 |
| 5,138,106 | 8/1992 | Wilmott et al. | 568/885 |
| 5,142,067 | 8/1992 | Wegman et al. | 549/326 |
| 5,155,086 | 10/1992 | Thakur et al. | 502/342 |
| 5,157,168 | 10/1992 | Wilmott et al. | 568/877 |
| 5,180,858 | 1/1993 | Fleckenstein et al. | 568/885 |
| 5,233,099 | 8/1993 | Tabata et al. | 568/885 |
| 5,233,100 | 8/1993 | Tabata et al. | 568/885 |
| 5,254,520 | 10/1993 | Sofianos | 502/307 |
| 5,324,871 | 6/1994 | Carduck et al. | 568/885 |
| 5,334,779 | 8/1994 | Kuo | 568/864 |
| 5,345,005 | 9/1994 | Thakur et al. | 568/885 |
| 5,364,986 | 11/1994 | Demmering et al. | 568/885 |
| 5,387,753 | 2/1995 | Scarlett et al. | 568/864 |
| 5,395,990 | 3/1995 | Scarlett | 568/864 |
| 5,395,991 | 3/1995 | Scarlett et al. | 568/864 |
| 5,463,143 | 10/1995 | Singleton et al. | 568/885 |
| 5,475,159 | 12/1995 | Singleton et al. | 568/885 |
| 5,478,789 | 12/1995 | Hattori et al. | 568/885 |

FOREIGN PATENT DOCUMENTS

| | | |
|---|---|---|
| 0424069A1 | 4/1991 | European Pat. Off. . |
| 0523818A2 | 1/1993 | European Pat. Off. . |

*Primary Examiner*—Joseph E. Evans
*Attorney, Agent, or Firm*—Pamela J. McCollough

[57] ABSTRACT

This invention relates to a process for the two-stage hydrogenation of methyl esters which comprises: a) contacting and reacting one or more detergent range methyl esters with hydrogen under predominantly liquid phase hydrogenation conditions at a temperature of less than about 230° C., in the presence of a catalyst comprising a copper compound, a zinc compound, and at least one compound selected from the group consisting of aluminum, zirconium, magnesium, a rare earth and mixtures thereof, to produce an alcohol product and a wax ester product, and b) contacting and reacting the wax ester product from step a) with hydrogen under predominantly liquid phase hydrogenation conditions at a temperature greater than about 220° C. in the presence of a catalyst comprising a copper compound, a zinc compound, and at least one compound selected from the group consisting of aluminum, zirconium, magnesium, a rare earth and mixtures thereof, to produce an alcohol product.

20 Claims, No Drawings

PROCESS FOR THE TWO-STAGE HYDROGENATION OF METHYL ESTERS

FIELD OF THE INVENTION

This invention relates to a process for the two-stage conversion of detergent range methyl esters to detergent range alcohols in a liquid phase hydrogenation process.

BACKGROUND OF THE INVENTION

The hydrogenation of carboxylic acids and carboxylic esters to alcohols is known in the art, and various methods and catalysts have been suggested for effecting the hydrogenation. A commonly practiced method involves the use of a copper-chromite-based hydrogenation catalyst. While copper chromite catalysts are successful and commercially available, the disposal of the spent copper chromite catalyst is a problem since chromium can exist in different oxidation states. Some of these oxidation states are reported to be toxic to humans.

Conversion of detergent range methyl esters or acids to the corresponding alcohols can be carried out at high pressures, i.e., above about 200 bars, or at lower pressures and moderate temperatures in the vapor phase, but the production rates are limited and the processes are economically unattractive. The conversion of methyl esters can also be carried out at lower pressures and moderate temperatures in the liquid phase at high space velocities and low hydrogen to feed ratios, but the process results in the formation of large amounts of wax esters and poor selectivity to the desired alcohol product.

It would therefore be advantageous to have an economically attractive process to hydrogenate detergent range methyl esters to the corresponding alcohols in the liquid phase which would yield an alcohol product of high quality.

SUMMARY OF THE INVENTION

This invention therefore provides a process for the two-stage hydrogenation of esters which comprises: a) contacting and reacting one or more detergent range methyl esters with hydrogen under predominantly liquid phase hydrogenation conditions at a temperature of less than about 230° C., in the presence of a catalyst comprising a copper compound, a zinc compound, and at least one compound selected from the group consisting of aluminum, zirconium, magnesium, a rare earth and mixtures thereof, to produce an alcohol product and a wax ester product, and b) contacting and reacting the wax ester product from step a) with hydrogen under predominantly liquid phase hydrogenation conditions at a temperature greater than about 220° C., in the presence of a catalyst comprising a copper compound, a zinc compound, and at least one compound selected from the group consisting of aluminum, zirconium, magnesium, a rare earth and mixtures thereof, to produce an alcohol product.

It has been found that high purity alcohols can be obtained utilizing the two stage process of the present invention.

DESCRIPTION OF THE PREFERRED EMBODIMENTS

The present invention relates to a process for the two-stage hydrogenation of detergent range methyl esters to form fatty alcohols. In the first stage or first step of the process, detergent-range methyl esters are converted at high conversion rates, i.e., at least about 96%, into wax esters and fatty alcohols. The fatty alcohols are separated out by conventional means and the wax esters are used as feed for the second stage or second step of the process wherein the wax esters from the first stage are converted into fatty alcohols.

In the first stage of the process of the present invention, one or more detergent range methyl esters is contacted and reacted with hydrogen in the presence of a catalyst comprising mixtures of a copper compound, a zinc compound, and at least one compound selected from the group consisting of aluminum, zirconium, magnesium a rare earth and mixtures thereof.

As used herein, the term "detergent range methyl esters" refers to compounds, typically $C_6$ to $C_{22}$ compounds, which have been produced by ester exchange of natural oils, such as coconut oil, rape seed oil, palm kernel oil and palm oils. Examples of detergent range methyl esters include methyl decanoate (methyl caprate), methyl dodecanoate (methyl laurate), methyl tetradecanoate (methyl myristate), methyl hexadecanoate (methyl palmitate), methyl octadecanoate (methyl stearate), and methyl octadecenoate (methyl oleate). As used herein, "fatty alcohol" refers to an alcohol, preferably a linear alcohol, containing from about 6 to about 22 carbon atoms, preferably from about 10 carbon atoms to about 22 carbon atoms. Typical fatty alcohols produced by the two-stage hydrogenation process of the present invention include decanol, dodecanol, tetradecanol, hexadecanol, octadecanol, and the like, and mixtures thereof. As used herein, the term "wax esters" refers to compounds, typically $C_6$ to $C_{44}$ compounds, which have been produced by exchange of the product alcohol with the feed methyl ester, in situ. Examples of triglycerides which can be used as raw materials to form wax esters include natural oils, such as coconut oil, rape seed oil, and palm oils, and animal fats, such as lard, tallow and fish oil. Examples of wax esters include decyl decanoate (capryl caprate), dodecyl dodecanoate (lauryl laurate), tetradecyl tetradecanoate (myristyl myristate), hexadecyl hexadecanoate (palmityl palmitate), octadecyl octadecanoate (stearate or isostearate), octadecenyl octadecenoate (oleate, linoleate or linolenate), lauryl myristate, myristyl palmitate, oleyl laurate, and docosyl docosanoate (erucyl erucate).

The catalyst in both the first and second stages of the process of the present invention comprise mixtures of a copper compound, a zinc compound, and at least one compound selected from the group consisting of aluminum, zirconium, magnesium, a rare earth and mixtures thereof. The catalyst composition is prepared by a process which comprises co-precipitating from aqueous solution compounds of copper, zinc, and at least one of aluminum and/or zirconium and/or magnesium and/or rare earth, washing, drying and calcining the precipitate, and subsequently activating the calcined precipitate in a reducing atmosphere.

The copper content of the catalyst can vary over a wide range for example, from about 10 percent by weight to about 80 percent by weight, calculated as the oxide, basis the total weight of the catalyst. However, for an optimal combination of initial catalyst activity and catalyst stability, a copper content in the range of from about 25 percent by weight to about 75 percent by weight, calculated as the oxide, is preferred, especially from about 30 percent by weight to about 70 percent by weight, calculated as the oxide. All ratios specified herein are metal atoms unless otherwise noted.

The zinc content of the catalyst is typically in the range of from about 10 percent by weight to about 80 percent by weight, calculated as the oxide, basis the total weight of the catalyst. Preferably, the zinc content of the catalyst is in the range of from about 15 percent by weight to about 75 percent by weight, calculated as the oxide, especially from about 20 percent by weight to about 70 percent by weight, calculated as the oxide. The ratio of zinc to copper in the catalyst is generally in the range of from about 1:5 to about 5:1, and preferably in the range of from about 1:4 to about 2:1.

The catalyst additionally comprises at least one compound selected from the group consisting of aluminum, zirconium, magnesium, a rare earth and mixtures thereof.

When a rare earth compound is utilized, the rare earth content of the catalyst is typically in the range of from about 0.1 percent by weight to about 20 percent by weight, calculated as the oxide, basis the total weight of the catalyst. Preferably, the rare earth content of the catalyst is in the range of from about 0.2 percent by weight to about 15 percent by weight, calculated as the oxide, especially from about 0.3 percent by weight to about 10 percent by weight, calculated as the oxide.

As used herein, the terms "rare earth" and "lanthanide" refer to the series of elements with atomic numbers ranging from 57 (lanthanum) through 71 (lutetium). With regard to the rare earth (lanthanide) series, mixed metals are readily available commercially. For purposes of the present invention, the rare earth is selected from the group consisting of praseodymium, neodymium, yttrium, lanthanum, samarium, thorium, cerium and mixtures thereof, with lanthanum being preferred.

When the catalyst contains aluminum, the aluminum content of the catalyst is typically in the range of from about 0.05 percent by weight to about 30 percent by weight, calculated as the oxide, basis the total weight of the catalyst. Preferably, the aluminum content of the catalyst is in the range of from about 0.4 percent by weight to about 20 percent by weight, calculated as the oxide, especially from about 0.6 percent by weight to about 10 percent by weight, calculated as the oxide.

When the catalyst contains zirconium, the zirconium content of the catalyst is typically in the range of from about 0.05 percent by weight to about 30 percent by weight, calculated as the oxide, basis the total weight of the catalyst. Preferably, the zirconium content of the catalyst is in the range of from about 0.4 percent by weight to about 20 percent by weight, calculated as the oxide, especially from about 0.6 percent by weight to about 10 percent by weight, calculated as the oxide.

When the catalyst contains magnesium, the magnesium content of the catalyst is typically in the range of from about 0.05 percent by weight to about 30 percent by weight, calculated as the oxide, basis the total weight of the catalyst. Preferably, the magnesium content of the catalyst is in the range of from about 0.4 percent by weight to about 20 percent by weight, calculated as the oxide, especially from about 0.6 percent by weight to about 10 percent by weight, calculated as the oxide.

When mixtures of a rare earth and/or aluminum and/or zirconium and/or magnesium are utilized, the total amount present in the catalyst is typically in the range of from about 0.05 percent by weight to about 30 percent by weight, calculated as the oxide, basis the total weight of the catalyst. Preferably, the total amount present in the catalyst is in the range of from about 0.4 percent by weight to about 20 percent by weight, calculated as the oxide, especially from about 0.6 percent by weight to about 10 percent by weight, calculated as the oxide.

In one embodiment, the catalyst comprises copper, zinc and zirconium. In another embodiment, the catalyst comprises, copper, zinc and aluminum. In another embodiment, the catalyst comprises copper, zinc, aluminum and zirconium. In another embodiment, the catalyst comprises, copper, zinc and a rare earth. In another embodiment, the catalyst comprises copper, zinc, magnesium and a rare earth.

Various procedures can be utilized to prepare the catalysts utilized in the first and second stages of the process of the present invention. For example, individual solutions of the metals may be prepared and mixed together followed by the addition of an aqueous alkaline solution. Alternatively, a first aqueous solution comprising a copper or zinc salt and a second solution comprising a soluble base and at least one soluble salt of at least one second metal can be prepared, and these two solutions are then added simultaneously to a vessel containing water. In a preferred embodiment, the catalysts are prepared by co-precipitating from aqueous solution thermally decomposable compounds of copper, zinc, and rare earth and/or aluminum and/or zirconium and/or magnesium, washing the precipitate and calcining the precipitate to give the metal oxides. The catalyst precursor is subjected to a reduction treatment to give the active catalyst.

It is understood that the catalyst is usually handled and stored in the form of its precursor, which indeed is referred to in commerce as the "catalyst", although it is not the catalyst in the strict sense of the agent taking part in chemical reactions such as hydrogenation of methyl esters. Reduction of the precursor to the catalyst is normally carried out by the operator of the chemical process. The precursor may be in shapes, e.g., pellets, as required by the user of the catalyst, or may be in its condition before the shaping operation, e.g., as powder or lightly compressed powder.

The initial form in which the copper, zinc and rare earth and/or aluminum and/or zirconium and/or magnesium are employed is the oxide, although compounds which are readily converted to the oxide, e.g., the corresponding metal carbonates, are also suitable initially employed as these are converted to the oxide during pretreatment subsequent to the formation of the initially prepared catalyst composition. Pretreatment of the catalyst in hydrogen and operation of the catalyst in the reaction environment will cause at least partial reduction of some of the metals, such as copper, to lower oxidation states, and it is intended that catalysts with these reduced states will fall within the scope of this invention.

The reaction temperatures utilized in the first stage of the present invention are typically in the range of from about 170° C. to about 230° C., preferably in the range of from about 190° C. to 225° C., and more preferably in the range of from about 205° C. to 225° C. With respect to the reaction temperatures, it is important to ensure that the temperature does not exceed 230° C. At temperatures greater than 230° C., the paraffin make increases to unacceptable levels. The reaction pressures are typically in the range of from about 300 psig to about 2000 psig, preferably in the range of from about 400 psig to about 1500 psig, and more preferably in the range of from about 500 psig to about 1000 psig. Operation at these low reaction pressures is possible due to the high activity and selectivity of the catalysts. The molar ratio of hydrogen to methyl ester in the process of the present invention is in the range of from about 20:1 to about 700:1, preferably from about 50:1 to about 650:1, and more preferably, from about 100:1 to about 600:1. The process is generally carried out at a weight hourly space velocity (WHSV) in the range of from about 0.1 $hr^{-1}$ to about 5 $hr^{-1}$, preferably in the range of from about 0.1 hr$^{-1}$ to about 3 hr$^{-1}$. The time period required for reaction will vary according to the temperature utilized, the molar ratio of hydrogen to methyl ester, and the partial pressure of hydrogen.

The products produced in the first stage of the present process include fatty alcohols, wax esters, traces of paraffins and unreacted methyl esters. The fatty alcohols produced are typically separated by conventional means such as, for example, distillation, extraction, filtration, crystallization, and the like. The wax esters produced in the first stage are then subjected to subsequent treatment in the second stage of the process.

In the second stage of the process of the present invention, the wax ester product from the first stage is contacted and reacted with hydrogen under liquid phase hydrogenation conditions in the presence of a catalyst comprising a copper compound, a zinc compound, and at least one compound selected from the group consisting of aluminum, zirconium, magnesium, a rare earth and mixtures thereof. The second stage is carried out under "more severe" conditions than the first stage in order to more fully convert the wax esters to alcohols. These "more severe" conditions include at least one of the following: i) a higher temperature than that utilized in the first stage; ii) a higher hydrogen to feed molar ratio than that utilized in the first stage; and/or iii) a lower space velocity than that utilized in the first stage. Typically, the "more severe" conditions utilized include a combination of a higher hydrogen to feed molar ratio and a lower space velocity.

The catalyst in the second stage comprises a copper compound, a zinc compound, and at least one compound selected from the group consisting of aluminum, zirconium, magnesium, a rare earth and mixtures thereof. The relative amounts of catalyst and the various possible combinations of components of catalyst suitable for use in the second stage are the same as those set forth in the above catalyst discussion, and while the catalyst utilized in the second stage may be the same as that utilized in the first stage, it is also suitable to use a different catalyst in the second stage than that utilized in the first stage. For example, the catalyst may comprise copper, zinc and zirconium; copper, zinc and aluminum; copper, zinc, aluminum and zirconium; copper, zinc and a rare earth; or copper, zinc, magnesium and a rare earth. In a preferred embodiment, the catalyst utilized in the second stage comprises copper, zinc, and at least one rare earth compound.

The reaction temperatures utilized in the second stage of the process are typically in the range of from about 220° C. to about 240° C. preferably in the range of from about 220° C. to 235° C. and more preferably in the range of from about 225° C. to 235° C. The reaction pressures are typically in the range of from about 300 psig to about 2000 psig, preferably in the range of from about 400 psig to about 1500 psig, and more preferably in the range of from about 500 psig to about 1000 psig. Operation at these low reaction pressures is possible due to the high activity and selectivity of the catalysts. The molar ratio of hydrogen to wax ester in the process of the present invention is in the range of from about 20:1 to about 700:1, preferably from about 250:1 to about 650:1, and more preferably, from about 400:1 to about 600:1. The process is generally carried out at a weight hourly space velocity (WHSV) in the range of from about 0.1 hr$^{-1}$ to about 5 hr$^{-1}$, preferably in the range of from about 0.1 hr$^{-1}$ to about 3 hr$^{-1}$. The time period required for reaction will vary according to the temperature utilized, the molar ratio of hydrogen to wax ester, and the partial pressure of hydrogen.

The process of the present invention is typically carried out in a reactor, which may be a trickle bed reactor, a fixed bed gas-solid reactor, a packed bubble column reactor, a continuously stirred tank reactor or a slurry phase reactor. The process may be carried out batchwise or in continuous fashion. The reaction is carried out in a predominantly liquid phase. As used herein, the term "predominantly liquid phase" refers to a reaction in which greater than 50%, and approaching 100% of the reaction mixture (other than hydrogen) is in the liquid phase.

The fatty alcohol products produced in the process of the present invention are utilized in various applications, such as, for example, detergents such as laundry powders, laundry liquids, etc. and personal care products such as shampoos, etc.

An advantage of the present process is the conversion, i.e., greater than at least about 96 mole percent, and approaching 100%, basis methyl ester and wax ester, as well as the selectivity to fatty alcohols, i.e., greater than about 97 mole percent, and approaching 100%. The process also has advantages in that it produces very pure alcohols with very low levels of paraffins.

The ranges and limitations provided in the present specification and claims are those which are believed to particularly point out and distinctly claim the present invention. It is, however, understood that other ranges and limitations which perform substantially the same function in substantially the same manner to obtain the same or substantially the same result are intended to be within the scope of the present invention as defined by the specification and claims.

The invention is further described with reference to the following examples, which are intended to illustrate certain aspects of the invention, without limiting its broader scope. Illustrative Embodiments

EXAMPLE 1

Stage 1 of the Process

A. Catalyst Preparation

A solution of mixed nitrates, 96 grams (0.41 mole) of cupric nitrate, 60 grams (0.2 mole) zinc nitrate, 3.3 grams (0.008 mole) lanthanum nitrate in one liter of water was heated to 85° C. and placed in a dish and funnel. In a second funnel was placed a hot 50° C. 1 molar solution of ammonium carbonate of sufficient quantity to provide an excess over the metal nitrates. Two solutions were added simultaneously over a period of about 20 minutes to a vessel containing 1 liter of vigorously stirred distilled water at 65° C. The rates of addition were adjusted so as to maintain the pH of the mixture at about pH equal to about 6.5. After the addition had been completed the slurry was aged at 85° C. for 20 minutes and then allowed to settle and washed 5 times by decantation and reslurrying before being filtered and dried. The mixed carbonates were then calcined at 300° C. for 4 hours. The resulting oxide material was compressed isostatically at 20,000 lbs. and then crushed and sieved.

B. Process

The second stage of the process of the present invention was carried out in a laboratory reactor tube constructed of 316 stainless steel which included a thermowell. The tube had an outer diameter of 1 inch and an inner diameter of 0.6 inches. An equal volume of silicon carbide, (60–80 mesh) was mixed with 20.00 g of catalyst and centered in the reactor tube between two beds of enough 20 mesh silicon carbide to fill the reactor. The silicon carbide was used as a diluent. The reactor tube was placed in a four-zone furnace equipped with controlling thermocouples and its fittings were tightened. A multi-point thermocouple was inserted in to the thermowell to allow precise monitoring of the temperatures inside the reactor tube.

The catalyst was reduced by initiating a 10.0 L/Hr flow of approx. 5% hydrogen in nitrogen at a unit pressure of 135 psig. The reactor was heated at a rate of 60° C./Hr to 200° C. The catalyst was held at 200° C. for 17 hours. While maintaining the same flow rate, the catalyst was next reduced with hydrogen for an additional 8 hours.

After reduction, the unit pressure was raised to 600 psig by adjusting a backpressure regulator. The hydrogen flow was adjusted to a molar ratio of hydrogen to feed of 125:1. The reactor temperature was adjusted to 204.4 C. and the catalyst bed temperatures were allowed to equilibrate before the feed was introduced at a weight hourly space velocity 0.4. The feed was stored under nitrogen and, if necessary, heated to a temperature above its melting point before being pumped to the reactor through heated insulated lines to insure proper flow. Samples of the feed and products were analyzed by GC, NMR, IR, Mass Spectroscopy and elemental analysis.

The results for hydrogenation of pure methyl tetradecanoate (methyl myristate) are shown in Table 1.

Stage 2 of the Process

A. Catalyst Preparation

A solution of mixed nitrates, 96 grams (0.41 mole) of cupric nitrate, 60 grams (0.2 mole) zinc nitrate, 3.3 grams (0.008 mole) lanthanum nitrate in one liter of water was heated to 85° C. and placed in a dish and funnel. In a second funnel was placed a hot 50° C. 1 molar solution of ammonium carbonate of sufficient quantity to provide an excess over the metal nitrates. Two solutions were added simultaneously over a period of about 20 minutes to a vessel containing 1 liter of vigorously stirred distilled water at 65° C. The rates of addition were adjusted so as to maintain the pH of the mixture at about pH equal to about 6.5. After the addition had been completed the slurry was aged at 85° C. for 20 minutes and then allowed to settle and washed 5 times by decantation and reslurrying before being filtered and dried. The mixed carbonates were then calcined at 300° C. for 4 hours. The resulting oxide material was compressed isostatically at 20,000 lbs. and then crushed and sieved.

B. Process

The second stage of the process of the present invention was carried out in a laboratory reactor tube constructed of 316 stainless steel which included a thermowell. The tube had an outer diameter of 1 inch and an inner diameter of 0.6 inches. An equal volume of silicon carbide, (60–80 mesh) was mixed with 20.00 g of catalyst and centered in the reactor tube between two beds of enough 20 mesh silicon carbide to fill the reactor. The silicon carbide was used as a diluent. The reactor tube was placed in a four-zone furnace equipped with controlling thermocouples and its fittings were tightened. A multi-point thermocouple was inserted in to the thermowell to allow precise monitoring of the temperatures inside the reactor tube.

The catalyst was reduced by initiating a 10.0 L/Hr flow of approx. 5% hydrogen in nitrogen at a unit pressure of 135 psig. The reactor was heated at a rate of 60° C./Hr to 200° C. The catalyst was held at 200° C. for 17 hours. While maintaining the same flow rate, the catalyst was next reduced with hydrogen for an additional 8 hours.

After reduction, the unit pressure was raised to 600 psig by adjusting a backpressure regulator. The hydrogen flow was adjusted to a molar ratio of hydrogen to feed of 250:1. The reactor temperature was adjusted to 215.6 C. and the catalyst bed temperatures were allowed to equilibrate before the feed was introduced at a weight hourly space velocity (WHSV) of 0.15. The feed was stored under nitrogen and heated to a temperature above its melting point before being passed from a heated pump to the reactor through heated insulated lines to insure proper flow. Samples of the feed and products were analyzed by GC, NMR, IR, Mass Spectroscopy and elemental analysis.

The results for hydrogenation of pure tetradecyl tetradecanoate (myristyl myristate) are shown in Table 1.

EXAMPLE 2

Stage 1 of the Process
Stage 1 of the process was carried out according to the procedures set forth in Example 1, except that the temperature was 226.7° C.
Stage 2 of the Process
Stage 2 of the Process was carried out according to the procedures set forth in Example 1, except that the temperature was 226.7° C.

The results for hydrogenation of pure tetradecyl tetradecanoate (myristyl myristate) are shown in Table 1.

TABLE 1

| | | Catalyst Performance | | | | |
| | | | | | % m (average) | |
| Stage | Wax:Methyl Myristate | °C. | WHSV[a] | $H_2$:Feed[a,b] | Net Wax Conv. | ROH Yield |
| --- | --- | --- | --- | --- | --- | --- |
| Example 1: | | | | | | |
| 1 | 0:100 | 204.4 | 0.4 | 125:1 | −44.2 | 55.8 |
| 2 | 100:0 | 215.6 | 0.15 | 250:1 | 83.0 | 98.7 |
| Example 2: | | | | | | |
| 1 | 0:100 | 226.7 | 0.4 | 125:1 | −25.0 | 72.0 |
| 2 | 100:0' | 226.7 | 0.15 | 250:1 | 84.2 | 97.1 |

[a]On basis of methyl myristate, where present
[b]Mole:mole

As can be seen in Table 1 the present process results in conversions greater than 97 mole percent and product purities (of alcohol) greater than 95 mole percent. It can also be seen that the product yields of alcohol are greater than 95 mole percent, and that the paraffin make is less than 2 mole percent.

What is claimed is:

1. A process for the two-stage hydrogenation of methyl esters which comprises: a) contacting and reacting one or more detergent range methyl esters with hydrogen under predominantly liquid phase hydrogenation conditions at a temperature of less than about 230° C., in the presence of a catalyst comprising copper, zinc, and at least one metal selected from the group consisting of aluminum, zirconium, magnesium, and a rare earth metal, to produce an alcohol product and a wax ester product, separating the alcohol and b) contacting and reacting the wax ester product from step a) with hydrogen under predominantly liquid phase hydrogenation conditions at a temperature greater than about 220° C., in the presence of a catalyst comprising copper, zinc, and at least one metal selected from the group consisting of aluminum, zirconium, magnesium, and a rare earth metal, to produce an alcohol product.

2. The process of claim 1 wherein said detergent range methyl ester is selected from the group consisting of methyl decanoate (methyl caprate), methyl dodecanoate (methyl laurate), methyl tetradecanoate (methyl myristate), methyl hexadecanoate (methyl palmitate), methyl octadecanoate, methyl octadecenoate and mixtures thereof.

3. The process of claim 2 wherein said detergent range methyl ester is methyl myristate.

4. The process of claim 1 wherein said catalyst in step a) and step b) contains from about 10 percent by weight to about 80 percent by weight, calculated as the oxide, basis the total weight of the catalyst, of copper.

5. The process of claim 1 wherein said catalyst in step a) and step b) contains from about 10 percent by weight to about 80 percent by weight, calculated as the oxide, basis the total weight of the catalyst, of zinc.

6. The process of claim 1 wherein said catalyst in step a) contains copper, zinc and aluminum.

7. The process of claim 6 wherein said catalyst in step a) contains from about 10 percent by weight to about 80 percent by weight, calculated as the oxide, basis the total weight of the catalyst, of copper, from about 10 percent by weight to about 80 percent by weight, calculated as the oxide, basis the total weight of the catalyst, of zinc, and from about 0.05 percent by weight to about 30 percent by weight, basis the total weight of the catalyst, of aluminum.

8. The process of claim 1 wherein said catalyst in step a) contains copper, zinc and zirconium.

9. The process of claim 8 wherein said catalyst in step a) contains from about 10 percent by weight to about 80 percent by weight, calculated as the oxide, basis the total weight of the catalyst, of copper, from about 10 percent by weight to about 80 percent by weight, calculated as the oxide, basis the total weight of the catalyst, of zinc, and from about 0.05 percent by weight to about 30 percent by weight, basis the total weight of the catalyst, of zirconium.

10. The process of claim 1 wherein said catalyst in step a) contains copper, zinc, zirconium and aluminum.

11. The process of claim 10 wherein said catalyst in step a) contains from about 10 percent by weight to about 80 percent by weight, calculated as the oxide, basis the total weight of the catalyst, of copper, from about 10 percent by weight to about 80 percent by weight, calculated as the oxide, basis the total weight of the catalyst, of zinc, from about 0.05 percent by weight to about 30 percent by weight, basis the total weight of the catalyst, of zirconium, and from about 0.05 percent by weight to about 30 percent by weight, basis the total weight of the catalyst, of aluminum.

12. The process of claim 1 wherein said catalyst in step b) contains copper, zinc and a rare earth metal.

13. The process of claim 10 wherein said catalyst in step b) contains from about 10 percent by weight to about 80 percent by weight, calculated as the oxide, basis the total weight of the catalyst, of copper, from about 10 percent by weight to about 80 percent by weight, calculated as the oxide, basis the total weight of the catalyst, of zinc, and from about 0.1 percent by weight to about 20 percent by weight, calculated as the oxide, basis the total weight of the catalyst, of rare earth metal.

14. The process of claim 13 wherein said rare earth metal is selected from the group consisting of praseodymium, neodymium, yttrium, lanthanum, samarium, thorium, cerium and mixtures thereof.

15. The process of claim 14 wherein said rare earth is lanthanum.

16. The process of claim 1 wherein said catalyst in step b) contains copper, zinc, magnesium and a rare earth metal.

17. The process of claim 16 wherein said catalyst in step b) contains from about 10 percent by weight to about 80 percent by weight, calculated as the oxide, basis the total weight of the catalyst, of copper, from about 10 percent by weight to about 80 percent by weight, calculated as the oxide, basis the total weight of the catalyst, of zinc, from about 0.05 percent by weight to about 30 percent by weight, basis the total weight of the catalyst, of magnesium, and from about 0.1 percent by weight to about 20 percent by weight, calculated as the oxide, basis the total weight of the catalyst, of rare earth metal.

18. The process of claim 17 wherein said rare earth metal is selected from the group consisting of praseodymium, neodymium, yttrium, lanthanum, samarium, thorium, cerium and mixtures thereof.

19. The process of claim 1 wherein step a) of said process is carried out at a temperature in the range of from about 170° C. to about 230° C. and a pressure in the range of from about 300 psig to about 2000 psig.

20. The process of claim 1 wherein step b) of said process is carried out at a temperature in the range of from about 220° C. to about 240° C. and a pressure in the range of from about 300 psig to about 2000 psig.

* * * * *